US010232101B2

(12) United States Patent
Flanagan et al.

(10) Patent No.: US 10,232,101 B2
(45) Date of Patent: Mar. 19, 2019

(54) GAS EXCHANGE DEVICES AND RELATED METHODS OF USE

(71) Applicant: Boston Scientific Scimed, Inc., Maple Grove, MN (US)

(72) Inventors: Aiden Flanagan, Kilcolgan (IE); Bryan Allen Clark, Forest Lake, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 292 days.

(21) Appl. No.: 15/041,290

(22) Filed: Feb. 11, 2016

(65) Prior Publication Data
US 2016/0235902 A1 Aug. 18, 2016

Related U.S. Application Data

(60) Provisional application No. 62/115,528, filed on Feb. 12, 2015.

(51) Int. Cl.
*A61M 1/16* (2006.01)
*A61M 1/28* (2006.01)

(52) U.S. Cl.
CPC ........ *A61M 1/1678* (2013.01); *A61M 1/1698* (2013.01); *A61M 1/28* (2013.01); *A61M 1/1601* (2014.02); *A61M 2202/0208* (2013.01); *A61M 2202/0225* (2013.01); *A61M 2202/0476* (2013.01); *A61M 2230/005* (2013.01); *A61M 2230/202* (2013.01); *A61M 2230/205* (2013.01)

(58) Field of Classification Search
CPC .... A61M 1/1678; A61M 1/1698; A61M 1/16; A61M 1/14; A61M 1/28; A61M 2202/0476
See application file for complete search history.

(56) References Cited

U.S. PATENT DOCUMENTS

| 4,568,327 | A | * | 2/1986 | Seufert | A61M 1/16 210/646 |
| 4,631,053 | A | * | 12/1986 | Taheri | A61M 1/1678 128/DIG. 3 |
| 4,661,092 | A | | 4/1987 | Popovich et al. | |
| 4,671,287 | A | * | 6/1987 | Fiddian-Green | A61M 1/1678 600/363 |
| 5,277,176 | A | | 1/1994 | Habashi et al. | |
| 5,437,272 | A | | 8/1995 | Fuhrman | |

(Continued)

OTHER PUBLICATIONS

Hirschl et al., "Development and application of a simplified liquid ventilator", Jan. 1995, pp. 157-163, vol. 23, No. 1, Critical Care Medicine (8 pages).

(Continued)

*Primary Examiner* — Theodore J Stigell
*Assistant Examiner* — Hong-Van N Trinh
(74) *Attorney, Agent, or Firm* — Bookoff McAndrews, PLLC

(57) ABSTRACT

A gas exchange system may include an elongate member including a liquid circuit and configured to be inserted into a body lumen, and a gas exchanger in fluid communication with the elongate member. A gas transfer fluid may be disposed within the liquid circuit of the elongate member. The gas transfer fluid may be configured to absorb carbon dioxide from a body fluid disposed in the body lumen, and subsequently release the carbon dioxide in the gas exchanger.

17 Claims, 3 Drawing Sheets

(56) References Cited

U.S. PATENT DOCUMENTS

| | | | |
|---|---|---|---|
| 5,840,767 A | 11/1998 | Clark, Jr. | |
| 2003/0039582 A1* | 2/2003 | Chambers | A61M 1/1678 422/44 |
| 2004/0118407 A1 | 6/2004 | Kandler | |
| 2006/0264810 A1* | 11/2006 | Hattler | A61M 1/1678 604/26 |
| 2008/0014115 A1* | 1/2008 | Johns | A61M 1/1678 422/46 |

OTHER PUBLICATIONS

Kaisers et al., "Liquid Ventilation", 2003, pp. 143-151, vol. 91, The British Journal of Anaesthesia (9 pages).

Spiess, Bruce D., "Basic mechanisms of gas transport and past research using perfluorocarbons", Mar. 2010, pp. 23-28, vol. 40, No. 1, Diving and Hyperbaric Medicine (6 pages).

Mihelc et al., "Evaluation of a Respiratory Assist Catheter that Uses an Impeller Within a Hollow Fiber Membrane Bundle", 2009, pp. 569-574, vol. 55, American Society of Artificial Internal Organs (6 pages).

Terragni et al., "Extracorporeal lung support to remove carbon dioxide", 2012, pp. 142-152, vol. 55, European Respiratory Monograph (11 pages).

* cited by examiner

GAS EXCHANGE DEVICES AND RELATED METHODS OF USE

CROSS-REFERENCE TO RELATED APPLICATION(S)

This patent application claims the benefit under 35 U.S.C. § 119 to U.S. Provisional Patent Application No. 62/115,528, filed on Feb. 12, 2015, the entirety of which is incorporated herein by reference.

TECHNICAL FIELD

Various examples of the present disclosure relate generally to medical devices and related methods of use. More specifically, the present disclosure relates to gas exchange devices, systems, and methods for facilitating gas exchange in the body.

BACKGROUND

Chronic obstructive pulmonary disease (COPD) includes conditions such as, e.g., chronic bronchitis and emphysema. COPD currently affects over 15 million people in the United States alone and is currently the third leading cause of death in the country. The primary cause of COPD is the inhalation of cigarette smoke, responsible for over 90% of COPD cases. The economic and social burden of the disease is substantial and is increasing.

Chronic bronchitis is characterized by chronic cough with sputum production. Due to airway inflammation, mucus hypersecretion, airway hyperresponsiveness, and eventual fibrosis of the airway walls, significant airflow and gas exchange limitations result.

Emphysema is characterized by the destruction of the lung parenchyma. This destruction of the lung parenchyma leads to a loss of elastic recoil and tethering which maintains airway patency. Because bronchioles are not supported by cartilage like the larger airways, they have little intrinsic support and therefore are susceptible to collapse when destruction of tethering occurs, particularly during exhalation.

Acute exacerbations of COPD (AECOPD) often require emergency care and inpatient hospital care. An AECOPD is defined by a sudden worsening of symptoms (e.g., increase in or onset of cough, wheeze, and sputum changes) that typically last for several days, but can persist for weeks. An AECOPD is typically triggered by a bacterial infection, viral infection, or pollutants, which manifest quickly into airway inflammation, mucus hypersecretion, and bronchoconstriction, causing significant airway restriction.

Despite relatively efficacious drugs (long-acting muscarinic antagonists, long-acting beta agonists, corticosteroids, and antibiotics) that treat COPD symptoms, a particular segment of patients known as "frequent exacerbators" often visit the emergency room and hospital with exacerbations and also have a more rapid decline in lung function, poorer quality of life, and a greater mortality risk.

Reversible obstructive pulmonary disease includes asthma and reversible aspects of COPD. Asthma is a disease in which bronchoconstriction, excessive mucus production, and inflammation and swelling of airways occur, causing widespread but variable airflow obstruction thereby making it difficult for the asthma sufferer to breathe. Asthma is further characterized by acute episodes of airway narrowing via contraction of hyper-responsive airway smooth muscle.

The reversible aspects of COPD include excessive mucus production and partial airway occlusion, airway narrowing secondary to smooth muscle contraction, and bronchial wall edema and inflation of the airways. Usually, there is a general increase in bulk (hypertrophy) of the large bronchi and chronic inflammatory changes in the small airways. Excessive amounts of mucus are found in the airways, and semisolid plugs of mucus may occlude some small bronchi. Also, the small airways are narrowed and show inflammatory changes.

In asthma, chronic inflammatory processes in the airway play a central role in increasing the resistance to airflow within the lungs. Many cells and cellular elements are involved in the inflammatory process including, but not limited to, mast cells, eosinophils, T lymphocytes, neutrophils, epithelial cells, and even airway smooth muscle itself. The reactions of these cells result in an associated increase in sensitivity and hyperresponsiveness of the airway smooth muscle cells lining the airways to particular stimuli.

The chronic nature of asthma can also lead to remodeling of the airway wall (i.e., structural changes such as airway wall thickening or chronic edema) that can further affect the function of the airway wall and influence airway hyperresponsiveness. Epithelial denudation exposes the underlying tissue to substances that would not normally otherwise contact the underlying tissue, further reinforcing the cycle of cellular damage and inflammatory response.

In susceptible individuals, asthma symptoms include recurrent episodes of shortness of breath (dyspnea), wheezing, chest tightness, and cough. Currently, asthma is managed by a combination of stimulus avoidance and pharmacology.

In severe cases of COPD and in AECOPD, patients also can experience a build-up of carbon dioxide ($CO_2$), known as hypercapnia, which can create dangerous conditions such as acidosis (low pH of the blood). In respiratory-compromised lungs, blood returning to the heart may not have sufficient oxygen ($O_2$) content, and may have too much $CO_2$. These $O_2$ and $CO_2$ levels may affect the functioning of the patient, particularly during physical exertion. Low pH levels in the blood have been shown to correlate to the need for hospital readmission and higher mortality rates. $O_2$ is often administered to COPD patients with severe symptoms to treat hypoxemia. However, evidence suggests administration of $O_2$ can lead to high levels of $CO_2$ in the blood. End stage (GOLD IV) COPD patients have no other options except lung transplant. However, such patients are generally poor candidates for transplant procedures due to co-morbid conditions. Perfluorocarbons (PFCs) have been used experimentally for liquid ventilation (e.g., liquid PFC has been used to fill the lung instead of air, vapour, or mist) in patients with lung injury and/or acute respiratory distress, and neonates. Some studies show PFC use to be safe, but no substantial benefit has been observed when used in this way.

Extracorporeal Membrane Oxygenators (ECMOs) have been used for removing $CO_2$ in hypercapnic patients. Some are positioned outside the body and are supplied with blood from intra-venous and intra-arterial catheters. Other experimental attempts have placed a large gas exchange unit in the vena-cava. The gas exchange unit can be supplied with external air. However, this design has not been efficient enough to date for practical use.

Thus, a need exists for patients suffering from diseases of the lung. More specifically, a need exists for improved treatments for patients with hypercapnia to remove $CO_2$ from the blood.

SUMMARY OF THE DISCLOSURE

The present disclosure includes gas exchange devices for treating body fluids and related methods of use.

A gas exchange system may include an elongate member including a liquid circuit and configured to be inserted into a body lumen, and a gas exchanger in fluid communication with the elongate member. A gas transfer fluid may be disposed within the liquid circuit of the elongate member. The gas transfer fluid may be configured to absorb carbon dioxide from a body fluid disposed in the body lumen, and subsequently release the carbon dioxide in the gas exchanger.

The gas transfer fluid may be further configured to absorb oxygen while disposed in the gas exchanger, and subsequently release the oxygen to the body fluid. A distal end of the elongate member may include a membrane permeable to at least carbon dioxide and oxygen. A proximal end of the elongate member may include a membrane permeable to at least carbon dioxide and oxygen. The gas transfer fluid may be a perfluorocarbon or blood substitute. The gas exchange system may further include a sensor configured to monitor the oxygen content or the carbon dioxide content of the body fluid disposed within the body lumen. The gas exchange system may further include a pump configured to drive fluid flow through the elongate member, and a controller coupled to the pump. The controller may be configured to adjust the flow rate of the gas transfer fluid through the elongate member based on an input from the sensor. The controller may be configured to increase the flow rate of the gas transfer fluid through the elongate member if the carbon dioxide content of the body fluid is above a first threshold value or if the oxygen content of the body fluid is below a second threshold value. The gas exchange system may further include an oxygen source coupled to the gas exchanger, and a controller coupled to the oxygen source. The controller may be configured to adjust a flow of oxygen from the oxygen source to the gas exchanger based on an input from the sensor.

A gas exchange system may include a first elongate member configured to be inserted into a first body lumen, and a second elongate member configured to be inserted into a second body lumen. A coupling may fluidly connect the first elongate member to the second elongate member. The first elongate member, the second elongate member, and the coupling may form a liquid circuit. A gas transfer fluid may be disposed within the liquid circuit. The gas transfer fluid may be configured to absorb carbon dioxide from a body fluid disposed in the second body lumen, and subsequently release the carbon dioxide in the first body lumen.

The entireties of the first elongate member, the second elongate member, and the coupling may be configured to be disposed within a body of a patient. At least one of the first elongate member and the second elongate member may be a stent, sleeve, basket, balloon, or hollow cylinder. Both the first elongate member and second elongate member may include one or more lumens forming a portion of the liquid circuit. Outer surfaces of the first elongate member and the second elongate member may include membranes that are permeable to carbon dioxide and oxygen. At least one of the first and second elongate members may include a plurality of fingers. Each of the plurality of fingers may have a plurality of projections. The fingers and the projections may be hollow and may include a membrane that is permeable to carbon dioxide and oxygen.

A method for facilitating gas exchange in a body may include absorbing carbon dioxide from a body fluid disposed in a body lumen with a gas transfer fluid circulating in a liquid circuit, and releasing the carbon dioxide absorbed by the gas transfer fluid outside of the body. Carbon dioxide may be released by the gas transfer fluid in a gas exchanger. The method may further include oxygenating the gas transfer fluid in the gas exchanger. The method may further include transferring oxygen from the gas transfer fluid to the body fluid disposed in the body lumen. The carbon dioxide from the body fluid may be transferred through a membrane to the gas transfer fluid.

A method for facilitating gas exchange in a body may include absorbing carbon dioxide from a body fluid disposed in a first body lumen with a gas transfer fluid disposed within a first elongate member disposed in the first body lumen, and transporting the gas transfer fluid with the absorbed carbon dioxide from the first elongate member to a second elongate member disposed in a second body lumen. The method also may include transferring the absorbed carbon dioxide from the gas transfer fluid to air flowing through the second body lumen.

The method may further include absorbing oxygen from the air flowing through the second body lumen with the gas transfer fluid disposed in the second elongate member, transporting the oxygenated gas transfer fluid to the first elongate member, and transferring the absorbed oxygen from the gas transfer fluid to the body fluid flowing through the first body lumen.

BRIEF DESCRIPTION OF THE FIGURES

The accompanying drawings, which are incorporated in and constitute a part of this specification, illustrate various examples and together with the description, serve to explain the principles of the disclosed examples.

DETAILED DESCRIPTION

Reference will now be made in detail to examples of the present disclosure, examples of which are illustrated in the accompanying drawings. Wherever possible, the same reference numbers will be used throughout the drawings to refer to the same or like parts.

Figure 1:
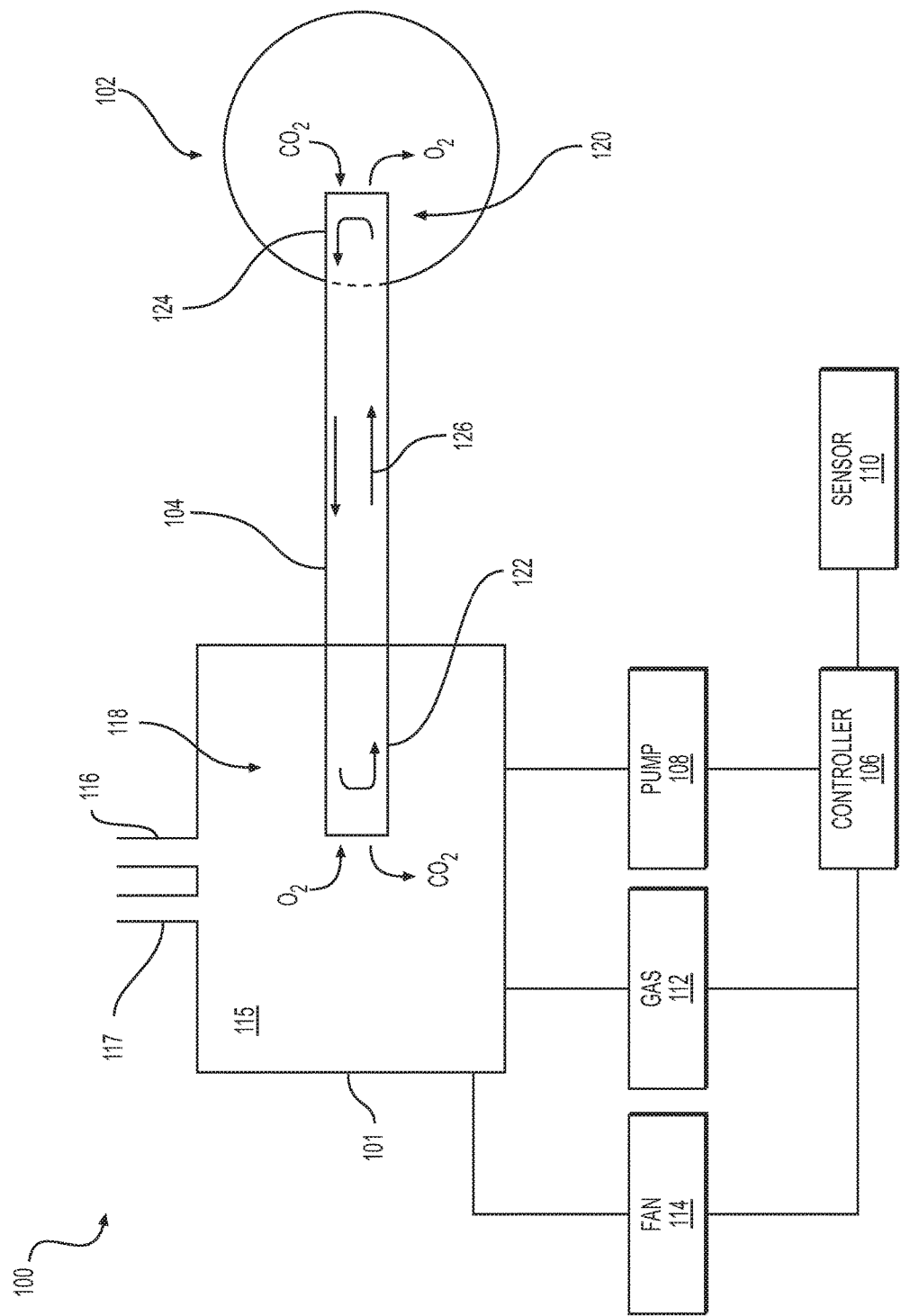
FIG. 1 is a schematic view of a gas exchange system in accordance with an example of the present disclosure.

A system 100 is shown in FIG. 1. System 100 may include a gas exchanger 101 that is configured to be at least partially inserted into a patient to facilitate gas exchange in a body lumen 102. Gas exchanger 101 and body lumen 102 may be coupled to one another by an elongate member 104. System 100 also may include one or more of a controller 106, a pump 108, a sensor 110, a gas source 112, and a circulating device 114, operatively coupled to one or both of gas exchanger 101 and elongate member 104.

Gas exchanger 101 may be disposed outside of the body, on the body, implanted within the body, or some combination of the above, if desired. Gas exchanger 101 may include a volume 115 that is configured to form a gas exchange interface with one or more of elongate member 104 and an external environment (e.g., ambient air). Volume 115 may be coupled to the outside environment via an inlet 116 and an outlet 117, or other suitable opening or conduit.

Elongate member 104 may be a shaft, catheter, tube, or other suitable elongate member, and may include a proximal end 118, and a distal end 120. Elongate member 104 may be formed from one or more biocompatible materials, such as, e.g., HDPE, silicone, polyurethane, ETFE, SIBS, PIB-PUR, or any other suitable medical grade polymers, and may be flexible and configured to extend through tortuous anatomy. Proximal end 118 may include a membrane 122 that forms a gas exchange interface with volume 115 of gas exchanger 101 and/or the external environment. A membrane 124 may be disposed at distal end 120 of elongate member 104, and may form a gas exchange interface with body lumen 102. Membranes 122 and 124 may be any suitable semi-permeable membrane formed of, e.g., silicones, urethanes, PTFE, expanded PTFE, PFA, LDPE, HDPE, polyamide, or other materials that are permeable to oxygen and carbon dioxide. Membranes 122, 124 may be configured to allow for the selective transfer of gases between fluids located on different sides of the membranes 122, 124. Membranes 122, 124 may include microfibers or microtubes (e.g., formed by electrospinning among other techniques) to increase gas exchange surface areas. In another example, membranes 122, 124 may include dual-walled membranes with a thin layer of a gas exchange fluid (e.g., a fluid 126) disposed between the membrane layers to increase gas exchange efficiency. Membranes 122, 124 may have relatively high membrane areas and thin walls, contributing to a relatively large surface area and greater gas exchange for the size of the device. Fluid 126 also may be circulated through elongate member 104 in a closed or partially-closed liquid circuit of gas exchanger 101. That is, fluid 126 may not exit elongate member 104 or gas exchanger 101 during normal operation and/or during gas exchange. In some examples, only gases may be transferred into or out of system 100. Elongate member 104 also may include one or more lumens (not shown) that are configured to convey or circulate fluid between proximal end 118 and distal end 120. Thus, fluid 126 may serve to promote gas exchange between an external environment (e.g., ambient air) and/or a concentrated gas source (e.g., an $O_2$ source), and the blood or body fluid of a patient. In some examples, the gas exchange surface (e.g., membranes 122, 124) of elongate member 104 may be formed as a stent, balloon, sleeve, or other suitable member.

Fluid 126 may be capable of transporting O2, CO2, and other gases. In one example, fluid 126 may be a perfluorocarbon (PFC), a blood substitute, hemoglobin-based oxygen carriers (HBOC), and perfluorocarbon-based oxygen carriers (PFBOC), hemopure, oxyglobin, polyheme, hempspan, dextran-hemoglobin, hemotech, or another suitable fluid. In some examples, by confining the fluid in a closed circuit (e.g., elongate member 104), relatively high concentrations of fluid 126 may be used, improving the gas transporting properties of system 100. High gas transport efficiencies may be achieved across membranes 122, 124, into and out of the fluid 126 circulating through elongate member 104. Fluid 126 may not chemically bind gas molecules, but may hold the gas molecules by enhanced solubility, thereby improving gas diffusion speed. In alternative examples, fluid 126 may chemically bind gas molecules, or may both chemically bind gas molecules and hold the gas molecules by enhanced solubility.

Fluid 126 may have an O2 solubility of 50 ml per 100 ml liquid (at atmospheric pressure), and a CO2 solubility of 198 ml per 100 ml liquid (at atmospheric pressure). Other suitable ranges are also contemplated. In at least some patients, blood may carry $O_2$ at 20 ml/100 ml because the $O_2$ may bind to hemoglobin. However, dissolved $O_2$ may be only 0.003 ml/100 ml. However, $CO_2$ may be dissolved in venous blood at a level of 3 ml/100 ml. Therefore, with respect to $O_2$ and $CO_2$, fluid 126 may have a higher a higher solubility than blood, even including the chemical binding of $O_2$ to hemoglobin. This, at equilibrium partial pressure of $O_2$, fluid 126 may act as a source of $O_2$, and as a sink for $CO_2$. Thus, fluid 126 may be a highly efficient and potent fluid for gas transport and exchange, which may enable miniaturization of the system 100. Providing fluid 126 as an intermediate medium between, e.g., blood and air may create a more effective gas transfer mechanism, as fluid 126 may serve as a reservoir of $O_2$, and a sink for $CO_2$. In some examples, system 100 may be made more efficient by supplying pure or highly concentrated $O_2$ gas at the interface between volume 115 and membrane 122. In some examples, the efficient gas transfer abilities of fluid 126 may allow system 100 to have a relatively small gas transfer interface surface area. Fluid 126 may additionally or alternatively include a suspension of microshells, nanoshells, or micelles that contain gas transport particles (e.g., PFC). In yet another example, fluid 126 may include a pure PFC emulsion without shells.

A controller 106 may be operatively coupled to gas exchanger 101 and/or elongate member 104. Controller 106 may be configured to optimize gas transfer through the patient based on algorithms and/or inputs from one or more sensors 110. In some examples, the controller 106 may include a processor that is generally configured to accept information from the system and system components, and process the information according to various algorithms to produce control signals for controlling pump 108, gas source 112, and circulating device 114. The processor may accept information from the system and system components, process the information according to various algorithms, and produce information signals that may be directed to visual indicators, digital displays, audio tone generators, or other indicators of, e.g., a user interface, in order to inform a user of the system status, component status, procedure status or any other useful information that is being monitored by the system. The processor may be a digital IC processor, analog processor or any other suitable logic or control system that carries out the control algorithms. In some examples, controller 106 may record treatment parameters such as, e.g., sensor data, flow rates of fluid 126, and other suitable treatment parameters so that they may be accessed for concurrent or subsequent analysis.

In some examples, controller 106 may be implanted subcutaneously. Alternatively, controller 106 may be disposed outside of the patient, but otherwise in communication with pump 108, sensors 110, gas source 112, circulating device 114, and other devices, through suitable communication mechanisms such as, e.g., wireless, IR, Bluetooth, or another suitable communication mechanism. In some examples, controller 106 may be configured to communicate with other instruments such as, e.g., diagnostic instruments, tablets, computers, cell phones, servers, or other instruments to transmit and receive data, instructions, or other suitable information. The communication of controller 106 with external devices may allow third parties (e.g., care providers or physicians) to observe the health condition of a patient.

Pump 108 may be coupled to elongate member 104, and may be configured to drive fluid 126 through the closed or partially-closed liquid circuit of elongate member 104. Pump 108 may be controlled by controller 106, or another suitable controller. Pump 108 may be any suitable pump, such as, e.g., a peristaltic pump, piston pump, motorized pump, microfluidic pump, infusion pump, or the like. Pump 108 may be powered by electrical power, mechanical power, chemical power, or another suitable mechanism. In one example, pump 108 may be powered by an energy harvesting device that may be energized by, e.g., body movements, breathing, or the like. In some examples, pump 108 may include redundant power sources (e.g., multiple batteries). Pump 108 may include a source (e.g., a reservoir) of fluid 126 to be circulated through elongate member 104. In some examples, pump 108 may include a plurality of reservoirs to hold a plurality of fluids 126.

One or more sensors 110 may be operatively coupled to controller 106. Sensor 110 may be a transcutaneous sensor configured to monitor $CO_2$ and/or $O_2$ levels in the blood. Controller 106 may be configured to adjust the flow rate of fluid 126 and/or the rate of gas (e.g., $O_2$) expelled by gas source 112 into volume 115 to maintain consistent levels of $O_2$ and $CO_2$ in the blood or other bodily fluid (e.g., $PaO_2$>95 mmHg, $PaCO_2$<40 mmHg, and PH>7.35 to avoid acidemia). In one example, sensor 110 may include an electrochemical electrode configured to measure the partial pressure of $CO_2$ ($P_{tcCO2}$). In another example, sensor 110 may include a light emitter and sensor (e.g., a pulse oximeter) that is configured to measure $O_2$ saturation $SpO_2$. Sensor 110 also may include a heating element for increased local perfusion. That is, if sensor 110 is making measurements across a tissue membrane (e.g., skin), lower body temperatures may cause vasoconstriction which reduces local blood supply from which sensor 110 may take measurements from. The vasoconstriction may result in inaccurate measurements or may prohibit measurements from being taken at all. Heating the local tissue may minimize vasoconstriction. In another example, sensor 110 may be incorporated into membrane 122 or 124, and measurements may be taken across the membrane film in contact with the blood or body fluid.

Gas source 112 may be a reservoir or other source of $O_2$ or another suitable gas. In some examples, controller 106 may control the flow rate of $O_2$ into volume 115 based on an input of sensor 110. For example, if sensor 110 indicates that $O_2$ levels are relatively low within the blood and/or body fluid of the patient, controller 106 may increase the flow rate of $O_2$ from gas source 112 into volume 115 of gas exchanger 101 (e.g., the flow rate of $O_2$ may be set at a first flow rate). In another example, if sensor 110 indicates that $CO_2$ levels are relatively high in the blood and/or body fluid of the patient, controller 106 may decrease the flow rate of $O_2$ from gas source 112 (e.g., the flow rate of $O_2$ may be set at a second flow rate that is lower than the first flow rate). In yet another example, if sensor 110 indicates that $O_2$ levels in the blood and/or body fluid are relatively low, but that $CO_2$ levels are relatively high, controller 106 may set the flow rate of $O_2$ to a third flow rate that is between the first and second flow rates in order to balance the competing concerns of oxygenating the patient and reducing acidosis in the body. Controller 106 may adjust the flow rate of $O_2$ based upon a feedback mechanism, such as, e.g., a PID feedback loop or a fuzzy logic controller, among others. In some examples, gas source 112 may not be controlled by controller 106, but instead may be controlled by a separate controller, or may be controlled manually by an operator. Further, if sensor 112 indicates that pH levels are too low, controller 106 may adjust the flow rate of gas source 112.

Circulating device 114 may be any suitable device, such as, e.g., a fan, configured to increase the flow of ambient air and/or $O_2$ in volume 115. Circulating device 114 may be operatively coupled to controller 106, and may be controlled in a substantially similar manner as gas source 112. Circulating device 114 may be disposed in one or more of volume 115, inlet 116, and outlet 117, of gas exchanger 101. For example, controller 106 may set the flow rate of the circulating device 114 to operate at a first parameter in the same or similar conditions that cause the controller 106 to set the gas source 112 to the first flow rate, to a second parameter in the same or similar conditions that cause the controller 106 to set the gas source 112 to the second flow rate, and to a third parameter in the same or similar conditions that cause the controller 106 to set the gas source 112 to the third flow rate. In some examples, the parameter may be the speed of the circulating device 114, or another suitable parameter. Increasing the speed of the circulating device may increase the rate at which $O_2$ is transferred into the blood.

In one example, system 100 may be used to facilitate gas exchange in the blood. System 100 may be configured to deliver $O_2$ and/or other gases to the blood, while simultaneously removing $CO_2$ and/or other gases from the blood as described above. Elongate member 104 may be positioned into a vessel, e.g., the vena cava, the subclavian vein, the jugular vein, or any other large vein, due to the relatively high levels of $CO_2$ in the venous blood. Elongate member 104 may be inserted percutaneously or through a valve that enters the blood supply, which may facilitate replacement of elongate member 104.

System 100 also may be used to facilitate gas exchange with visceral or lymphatic fluid located in the space between organs (e.g., the peritoneal cavity or the abdominal cavity). System 100 also may be used to facilitate gas exchange with pleural fluid located in the pleural cavity. System 100 may be configured to extract $CO_2$ and/or other gases from the visceral fluid, lymphatic fluid, or pleural fluid. In some examples, a fluid suspension or emulsion of microparticles containing one or more fluids 126 may be directly injected into the peritoneal cavity, the abdominal cavity, or the pleural cavity. The microparticles may be left in the body for a predetermined amount of time to perform gas exchange with the visceral fluid, the lymphatic fluid, or the pleural fluid. Alternatively, an operator may extract the microparticles after a sensor determines that the $CO_2$ content of the visceral fluid, the lymphatic fluid, or the pleural fluid is below an acceptable threshold. In some examples, pump 108 may drive the motion of fluid 126 in elongate member 104. In other examples, such as when the pleural fluid is being treated, breathing pressure changes in the pleural cavity may facilitate the motion of fluid 126 in elongate member 104.

System 100 also may be used to facilitate gas exchange in the intestinal tract. That is, elongate member 104 may be inserted into the intestinal tract (which is in contact with a large volume of blood), to facilitate gas exchange in the body. In other examples, system 100 may be used for localized organ gas transfer. That is, elongate member 104 can be inserted directly into an organ. For example, elongate member can be inserted into the kidney when, e.g., renal failure is imminent due to respiratory failure. In other examples, elongate member 104 can be inserted into transplant organs such as the lung or heart. In yet another example, system 100 may be used with patients suffering from peripheral ischemia (e.g., diabetics). For example, elongate member 104 may be inserted directly into a targeted microvasculature (e.g., the leg microvasculature) experiencing poor blood oxygenation to oxygenate the systemic blood. In yet another example, system 100 may be used to oxygenate anoxic tissue, such as, for example, Glioma tumors.

Figure 2:
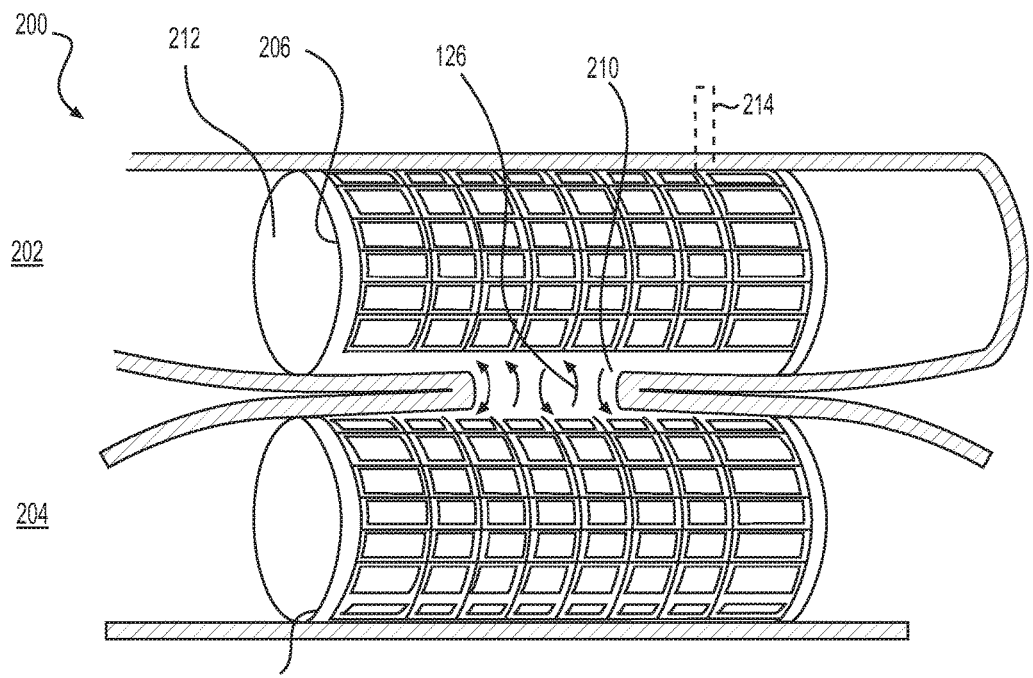
FIGS. 2-4 are schematic views of gas exchange devices in accordance with other examples of the present disclosure.

A gas exchanger 200 is shown in FIG. 2. Gas exchanger 200 may be an implant disposed within a first body lumen 202 and a second body lumen 204. First body lumen 202 may be an airway, such as, e.g., the left or right bronchus, or a higher generation airway. Second body lumen 204 may be a blood vessel, such as, e.g., the pulmonary artery or the azygos vein, among others. In some examples, gas exchanger 200 may be fully implantable within a patient (e.g., an entirety or substantial entirety of gas exchanger 200 may be enclosed within the body of the patient).

Gas exchanger 200 may include a first elongate member 206, a second elongate member 208, and a coupling 210 that may fluidly connect first elongate member 206 to second elongate member 208. First elongate member 206 may be configured to move between a collapsed configuration and an expanded configuration. In some examples, first elongate member 206 may be a self-expanding stent (e.g., a braided stent). In other examples, first elongate member 206 may be formed as a basket, sleeve, balloon, hollow cylinder, or another suitable shape. At least a portion of first elongate member 206 may include a lumen or reservoir through which fluid 126 may flow through or circulate. For example, when first elongate member 206 is a stent, one or more of the struts of the stent each may define one or more lumens. In other examples, a substantial entirety of first elongate member 206 may define a lumen. For example, when first elongate member 208 is a hollow cylinder, a substantial entirety of the outer surfaces of the hollow cylinder may define a ring-shaped lumen through which fluid 126 may flow or circulate.

The outer surfaces of first elongate member 206 (e.g., the surfaces in contact with body tissues and fluids) may include a membrane substantially similar to membranes 122 and 124 described with reference to FIG. 1. The membranes of the outer surfaces may allow for the transfer of gases between fluids disposed outside of first elongate member 206 (e.g., blood, body fluid, ambient air, or other suitable fluids), and fluid 126 disposed within first elongate member 206. A conduit or lumen 212 may extend longitudinally through first elongate member 206 for the transmission of body fluid, and may improve the gas transfer properties of first elongate member 206.

Second elongate member 208 may be substantially similar to first elongate member 206. Alternatively, second elongate member 208 may have one or more different features than first elongate member 206. For example, because first elongate member 206 may not be submerged in liquid, it may be able to accommodate additional surface area-enhancing structures, lattices, or the like, without increasing the risk of blood clotting. Further, as second elongate member 208 may be disposed in blood, second elongate member may include non-thrombogenic materials. Thus, the lumens defined by first elongate member 206, second elongate member 208, and coupling 210 may define a closed liquid circuit through which fluid 126 may continuously flow. Elongate member 208 also may be used within another device that performs a different function in the body where anoxic conditions could occur (e.g., ischemic tissue behind an aortic valve, a covered stent in an abdominal aortic aneurysm graft, or an ischemic tissue area in the body (leg, heart, brain, or the like)), in order to supply oxygen to these areas.

In one example, coupling 210 may extend through tissues defining first body lumen 202, and through tissues defining second body lumen 204. First elongate member 206 may be disposed in first body lumen 202, while second elongate member 208 may be disposed through second body lumen 204. Fluid 126 that flows through second elongate member 208 may be configured to absorb $CO_2$ disposed in a body fluid (e.g., blood) flowing in second body lumen 204. The fluid 126 flowing through second elongate member 208 also may be configured to transfer O2 (or another substance) to the body fluid flowing through body lumen 204. The deoxygenated and CO2-carrying fluid 126 then may flow from second elongate member 208, through coupling 210, to first elongate member 206. While disposed in first elongate member 206, the deoxygenated fluid 126 may be re-oxygenated by gas exchange with ambient air and/or supplemental O2 inhaled or otherwise ventilated through the patient. The fluid 126 flowing through first elongate member 206 may further transfer CO2 absorbed from second body lumen 204, to ambient air or another gas, flowing through first body lumen 202. The re-oxygenated and CO2-scrubbed fluid 126 then may flow from first elongate member 206, through coupling 210, to second elongate member 208. It is further contemplated that coupling 210 may include at least two lumens. For example, one lumen may facilitate fluid transfer from first elongate member 206 to second elongate member 208, while another lumen may facilitate fluid transfer in the opposite direction. First and second body lumens 202 and 204 may be two liquid-containing vessels, such as, e.g., a vein and artery, an artery and the peritoneal cavity, an artery and the pericardium, or the like. The gas/substance transfer can be enhanced in an artery by the mechanical movement created by the pulse (or if in the body by the body movement (lung, heart, legs, muscles etc.). In this case the stent may be flexible and elastic, and may move with the pulse expansion of the artery causing a subsequent movement of fluid within the first and/or second elongate members 206 and 208. Fluid flow in one direction may be facilitated by one way valves creating a circuit.

Gas exchanger 200 also may be operatively coupled to one or more of a controller, pump, sensor, or other suitable device (such as, e.g., controller 106, pump 108, and sensor 110 described with reference to FIG. 1). Further, while a pump 108 may drive fluid 126 through gas exchanger 200, it is also contemplated that fluid 126 may be driven by body motion, valves, heartbeats, or by pure diffusion. That is, the compression and expansion resulting breathing may cause the fluid 126 to flow through a series of one-way valves.

Gas exchanger 200 also may be refillable via a conduit 214 that is coupled to, e.g., a port, valve, septum, or other suitable member accessible at or beneath the skin. Conduit 214 may be coupled to one or more of first elongate member 206, second elongate member 208, and coupling 210. For example, fluid 126 may be replaced if it is determined that it is not effectively removing $CO_2$ from the blood. This may occur if the $CO_2$ is not being adequately removed from the fluid 126 flowing through first elongate member 206. Such determinations may be made by measurements taken by, e.g., sensor 110.

In the example shown in FIG. 2, both of first elongate member 206 and second elongate member 208 may be connected to coupling 210 at a respective center portion of each of first elongate member 206 and second elongate member 208. That is, holes or conduits in the sides of first elongate member 206 and second elongate member 208 may be connected by coupling 210. However, it is also contemplated that one or more of first elongate member 206 and second elongate member 208 may be connected to coupling 210 at another suitable location, such as, e.g., an end surface of each of first elongate member 206 and second elongate member 208.

Figure 3:
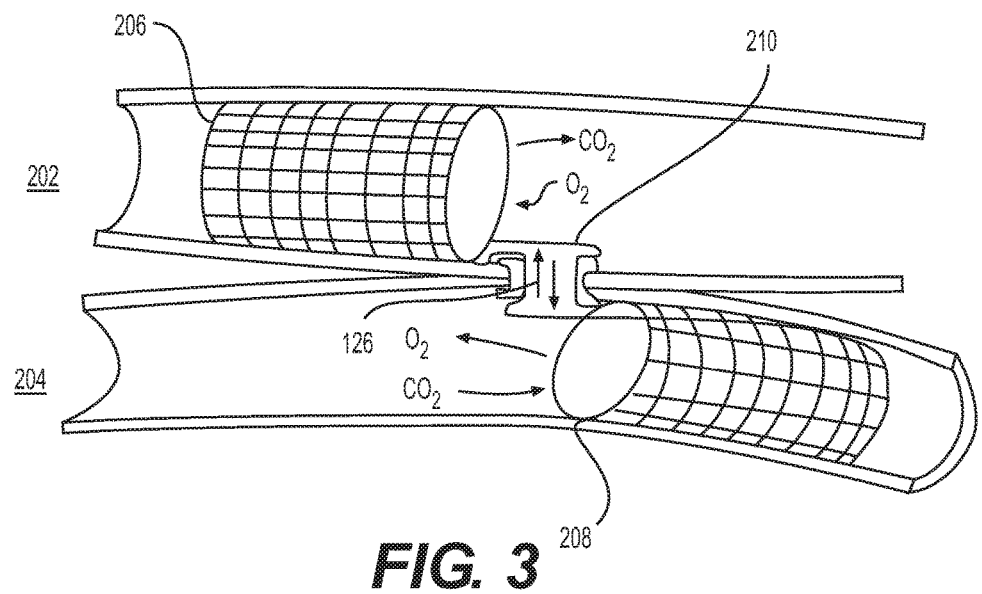

In the example shown in FIG. 3, first elongate member 206 may be connected to coupling 210 at an end surface of first elongate member 206, and may extend away from coupling 210 in a first direction. Further, second elongate member 208 also may be connected to coupling 210 at an end surface of second elongate member 208, and may extend away from coupling 210 in a second direction that is opposite to the first direction.

Figure 4:
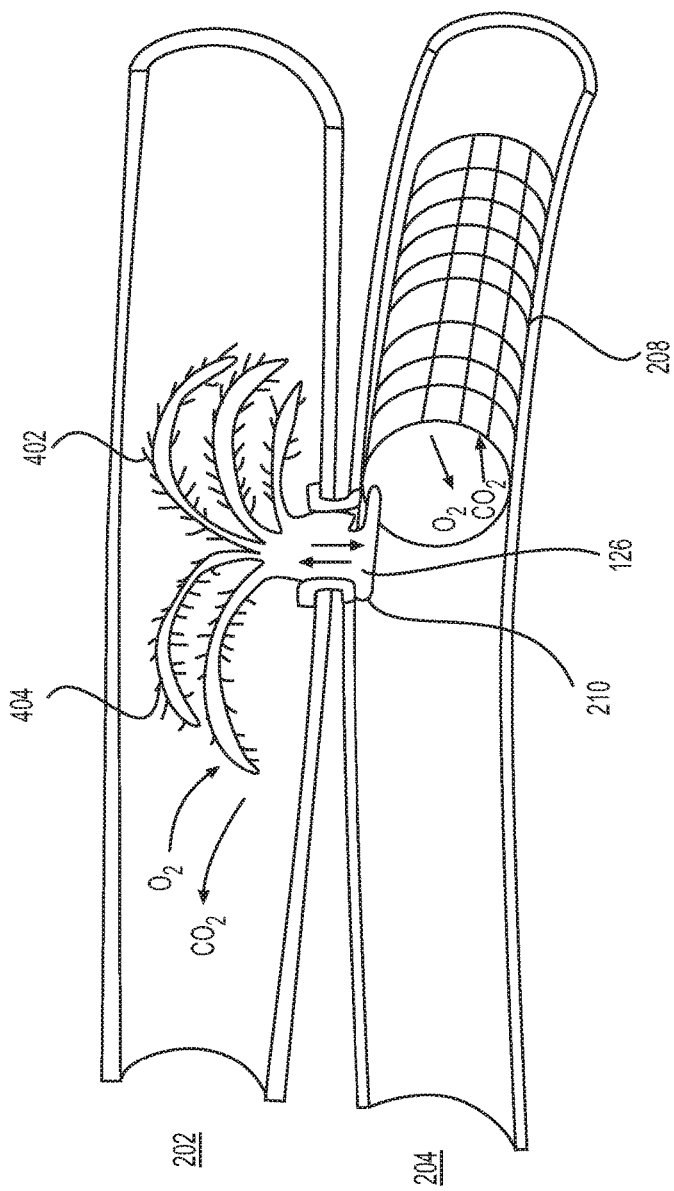

It is also contemplated that one or more of first and second elongate members 206 and 208 may be substituted for alternative gas exchange mechanisms. In the example of FIG. 4, first elongate member 206 may be replaced by one or more fingers 402 that extend away from coupling 210. Fingers 402 may be curvilinear or may be formed in another suitable shape. One or more of fingers 402 may include a plurality of projections 404. Both fingers 402 and projections 404 may be hollow to allow for a fluid (e.g., fluid 126) to flow through in a substantially similar manner as described with reference to first elongate member 206 and second elongate member 208. It is also contemplated that second elongate member 208 may be replaced by one or more fingers 402 or other high surface area gas exchange members. In some examples, fingers 402 may extend longitudinally and parallel to the length of the lumen to reduce the risk of clot formation in the bloodstream. Fingers 402 may be configured so as not to endothelialize such that gas exchange efficiency does not diminish with time. Fingers 402 and projections 404 may sway within the lumen 202 with the flow of fluid through the lumen (e.g., similar to the movement of anemones in marine environments).

Some examples of the present disclosure describe implantable devices that can augment respiration in the body. The disclosed devices and methods may be applicable for COPD and all other acute or chronic conditions that impair the respiratory functions, such as, e.g., restrictive respiratory functions, obstructive respiratory functions, and/or ventilation/perfusion respiratory functions, which may cause respiratory failure. Other treatable conditions include acute conditions that compromise respiratory function and result in hypercapnic conditions, such as, e.g., acute respiratory distress syndrome, drug/alcohol overdose, spinal injury, and the like. Various types of respiratory failure contemplated to be treated by this disclosure include, but are not limited to COPD, asthma, pulmonary fibrosis, bronchiectasis, cancer, tuberculosis, pneumonia, and ARDS. The disclosed systems may aid gas exchange between an airway and deoxygenated and/or hypercapnic blood, thereby causing an increase in the $O_2$ content, and a decrease in the $CO_2$ content of the blood entering the lungs for respiration. Any suitable body fluid may be treated with the disclosed systems and methods, such as, e.g., venous blood, arterial blood, lymph fluid, and/or body fluids, among others.

After treatment with any of the disclosed devices, the blood returning to the heart or in general circulation may have increased $O_2$ levels and decreased $CO_2$ levels (as compared to gas levels in patients not using any of the disclosed devices), resulting in improved outcomes for treated patients.

The disclosed systems may be used pre-ventilator in some patients, potentially preventing intubation, and avoiding invasive mechanical ventilation. The disclosed systems may reduce breathing effort and correct acidosis, giving patients time to recover from acute decompensation, AECOPD, and heart failure (HF) decompensation. The disclosed systems also may be used during acute care of a patient on mechanical ventilation. Usage during mechanical ventilation may enable lung-protective (e.g., low-flow) ventilation, and may permit de-escalation of ventilator settings while simultaneously correcting acidosis. The disclosed systems may be used in patients exhibiting one or more of Acute Respiratory Distress Syndrome (ARDS), pneumonia, COPD, Acute Lung Injury (ALI), Traumatic Brain Injury, and acute severe refractory Asthma, among the other conditions described above. The disclosed systems also may be used to help patients wean off of a mechanical ventilator. That is, some patients present an un-weanable condition (e.g., are unable to breathe without the assistance of mechanical ventilation) due to tachypnea, progressive hypercapnia, and/or acidosis. The disclosed systems may be used as a bridge to lung transplant. In some examples, the disclosed systems may help respiratory patients retain mobility prior to a lung transplant procedure. In some examples, patients may remain mobile for any suitable period of time, such as, e.g., up to 32 days, although both smaller and larger time periods are also contemplated. The disclosed systems may be used in inter-hospital patient transfer emergencies, battleground evacuations of wounded military and/or civilian personnel, and/or during surgery (e.g., thoracic surgery) in respiratory compromised patients. At least some examples of the present disclosure may result in reduced hospital admissions or readmissions in respiratory compromised patients, and may reduce mortality.

Any aspect set forth in any example may be used with any other example set forth herein. The devices and apparatus set forth herein may be used in any suitable medical procedure, and may be advanced through any suitable body lumen and body cavity. For example, the apparatuses and methods described herein may be used through any natural body lumen or tract, or through incisions in any suitable tissue.

It will be apparent to those skilled in the art that various modifications and variations can be made in the disclosed systems and processes without departing from the scope of the disclosure. Other examples of the disclosure will be apparent to those skilled in the art from consideration of the specification and practice of the disclosure disclosed herein. It is intended that the specification and examples be considered as exemplary only. The following disclosure identifies some other examples.

We claim:

1. A gas exchange system, comprising:
   a first member configured to be inserted into a first body lumen;
   a second member configured to be inserted into a second body lumen, wherein at least one of the first member and the second member is self-expanding;
   a coupling fluidly connecting the first member to the second member, wherein the first member, the second member, and the coupling form a liquid circuit; and
   a gas transfer fluid disposed within the liquid circuit, wherein the gas transfer fluid is configured to absorb carbon dioxide from a body fluid disposed in the second body lumen, and subsequently release the carbon dioxide in the first body lumen;
   wherein an outer surface of the first member and an outer surface of the second member each includes at least one membrane that is permeable to carbon dioxide and oxygen.

2. The gas exchange system of claim 1, wherein an entirety of the gas exchange system is configured to be disposed within a body of a patient.

3. The gas exchange system of claim 2, wherein:
   an entirety of the gas exchange system is configured to be implanted and contained within a lung airway, a blood vessel, and tissue disposed between the lung airway and the blood vessel.

4. The gas exchange system of claim 1, wherein at least one of the first member and the second member is a stent.

5. The gas exchange system of claim 4, wherein the stent includes one or more struts, at least one of the one or more struts defining a lumen.

6. The gas exchange system of claim 1, wherein both the first member and second member include one or more lumens forming a portion of the liquid circuit.

7. The gas exchange system of claim 1, wherein at least one of the first and second members includes a plurality of fingers, each of the plurality of fingers having a plurality of projections, the plurality of fingers and the plurality of projections being hollow and including at least one membrane that is permeable to carbon dioxide and oxygen.

8. The gas exchange system of claim 1, further including a one-way valve within the liquid circuit, wherein the gas transfer fluid within the liquid circuit is configured to flow in only one direction, and the liquid circuit is a closed circuit.

9. The gas exchange system of claim 8, wherein an entirety of the gas exchange system is implantable within a body of a patient, and the gas transfer fluid of the liquid circuit is configured to be driven through the one-way valve by compression and expansion of the patient during breathing.

10. The gas exchange system of claim 1, wherein the second member includes non-thrombogenic material.

11. The gas exchange system of claim 1, wherein the gas transfer fluid is a perfluorocarbon or a blood substitute.

12. A gas exchange system, comprising
a first member configured to be inserted into a first body lumen, wherein the first member includes a first self-expanding stent having one or more first struts, at least one of the one or more first struts enclosing a first lumen, and an outer surface of the at least one of the one or more first struts including a first membrane that is permeable to oxygen and carbon dioxide;
a second member configured to be inserted into a second body lumen, wherein the second member includes a second self-expanding stent having one or more second struts, at least one of the one or more second struts enclosing a second lumen, and an outer surface of the at least one of the one or more second struts including a second membrane that is permeable to oxygen and carbon dioxide;
a coupling fluidly connecting the first member to the second member, wherein the first member, the second member, and the coupling form a closed liquid circuit; and
a gas transfer fluid disposed within the closed liquid circuit, wherein the gas transfer fluid is configured to absorb carbon dioxide from a body fluid disposed in the second body lumen and release the carbon dioxide in the first body lumen.

13. The gas exchange system of claim 12, wherein the first body lumen is an airway, the second body lumen is a blood vessel, and an entirety of the gas exchange system is configured to be implanted and contained within the airway, the blood vessel, and tissue disposed between the airway and the blood vessel.

14. The gas exchange system of claim 13, further including a one-way valve within the closed liquid circuit, wherein the gas transfer fluid within the closed liquid circuit is configured to flow in only one direction, and the gas transfer fluid of the closed liquid circuit is configured to be driven through the one-way valve by compression and expansion of a patient during breathing.

15. The gas exchange system of claim 14, wherein the gas transfer fluid is a perfluorocarbon or a blood substitute.

16. The gas exchange system of claim 15, wherein the second member includes non-thrombogenic material.

17. A gas exchange system, comprising:
a first member configured to be inserted into a first body lumen;
a second member configured to be inserted into a second body lumen, wherein at least one of the first member and the second member is self-expanding;
a coupling fluidly connecting the first member to the second member, wherein the first member, the second member, and the coupling form a liquid circuit; and
a gas transfer fluid disposed within the liquid circuit, wherein the gas transfer fluid is configured to absorb carbon dioxide from a body fluid disposed in the second body lumen, and subsequently release the carbon dioxide in the first body lumen,
wherein an entirety of the gas exchange system is configured to be implanted and contained within a lung airway, a blood vessel, and tissue disposed between the lung airway and the blood vessel.

* * * * *